(12) United States Patent
Meier et al.

(10) Patent No.: US 11,147,164 B2
(45) Date of Patent: Oct. 12, 2021

(54) PRINTED CIRCUIT BOARD ASSEMBLY OF AN IMPLANTABLE MEDICAL DEVICE

(71) Applicant: BIOTRONIK SE & Co. KG, Berlin (DE)

(72) Inventors: Roman Meier, Schonstett (DE); Dany Quahs, Rehau (DE); Jan Romberg, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 17/017,916

(22) Filed: Sep. 11, 2020

(65) Prior Publication Data

US 2021/0092849 A1    Mar. 25, 2021

(30) Foreign Application Priority Data

Sep. 20, 2019 (EP) .................................. 19198533

(51) Int. Cl.
| | |
|---|---|
| *H05K 1/18* | (2006.01) |
| *C09J 11/04* | (2006.01) |
| *C09J 183/04* | (2006.01) |
| *H05K 3/30* | (2006.01) |
| *A61B 5/0215* | (2006.01) |
| *C08K 7/20* | (2006.01) |

(52) U.S. Cl.
CPC .............. *H05K 1/181* (2013.01); *C09J 11/04* (2013.01); *C09J 183/04* (2013.01); *H05K 3/305* (2013.01); *A61B 5/0215* (2013.01); *A61B 2562/166* (2013.01); *C08K 7/20* (2013.01); *H05K 2201/0162* (2013.01); *H05K 2201/0209* (2013.01); *H05K 2201/10151* (2013.01)

(58) Field of Classification Search
CPC ........................................................ H05K 1/181
USPC .............................................................. 361/760
See application file for complete search history.

(56) References Cited

U.S. PATENT DOCUMENTS

| | | | |
|---|---|---|---|
| 2003/0043476 A1 | 3/2003 | Snively et al. | |
| 2015/0131240 A1* | 5/2015 | Kostelnik | H05K 1/189 |
| | | | 361/751 |
| 2019/0078002 A1* | 3/2019 | Ueda | C09J 11/00 |

FOREIGN PATENT DOCUMENTS

| | | |
|---|---|---|
| EP | 2852970 A1 | 4/2015 |
| EP | 3428600 A1 | 1/2019 |

(Continued)

OTHER PUBLICATIONS

European Search Report and Annex to the European Search Report on European Patent Application No. EP 19 19 8533.2, dated Jan. 8, 2020 (5 pages).

*Primary Examiner* — Stanley Tso
(74) *Attorney, Agent, or Firm* — Buchanan Ingersoll & Rooney PC

(57) ABSTRACT

A printed circuit board assembly of an implantable medical device comprises a printed circuit board and a sensor device that is arranged at the printed circuit board and joined to the printed circuit board by way of an adhesive layer. It is provided in the process that the adhesive layer is formed of an adhesive compound in which glass spheres are embedded. In this way, a printed circuit board assembly is provided which, in a simple, inexpensive manner, allows a sensor device to be joined to a printed circuit board for installation in a medical device, with advantageous mechanical decoupling and improved process reliability.

6 Claims, 4 Drawing Sheets

(56) References Cited

FOREIGN PATENT DOCUMENTS

| JP | 2006047287 A | 2/2006 |
| JP | 2015075422 A | 4/2015 |

\* cited by examiner

PRINTED CIRCUIT BOARD ASSEMBLY OF AN IMPLANTABLE MEDICAL DEVICE

CROSS-REFERENCE TO RELATED APPLICATIONS

This patent application claims the benefit of and priority to co-pending European Patent Application No. EP 19198533.2, filed on Sep. 20, 2019 in the European Patent Office, which is hereby incorporated by reference in its entirety.

TECHNICAL FIELD

The present invention relates to a printed circuit board assembly of an implantable medical device, to an implantable medical device, and to a method for producing a printed circuit board assembly of an implantable medical device.

BACKGROUND

A known printed circuit board assembly comprises a printed circuit board and a sensor device that is arranged at the printed circuit board and joined to the printed circuit board by way of an adhesive layer.

Such a printed circuit board assembly is an integral part of a medical device, such as of an implantable pressure sensor to be implanted in a patient, for example so as to monitor the blood pressure in a blood vessel, in particular in the region of the human heart, intravascularly or intracardially.

In such an implantable pressure sensor, a sensor device, which comprises, for example, a pressure membrane for measuring a fluid pressure, is arranged on a printed circuit board and enclosed by way of the printed circuit board in a housing of the medical device. The printed circuit board is attached to the housing and carries further electrical or electronic components, for example for the implementation electronics for preprocessing sensor signals that are recorded via the sensor device and are supplied as electrical signals to the electrical or electronic components.

When mounted, the printed circuit board, including the sensor device arranged thereon, is usually fixedly connected to a surrounding housing. As a result, mechanical stresses that are introduced into the printed circuit board via the housing can also lead to loading at the sensor device and, in some circumstances, can distort sensor signals, which is to be avoided.

So as to achieve mechanical decoupling of the sensor device from the printed circuit board, in particular along a plane directed parallel to the surface of the printed circuit board, the sensor device is integrally joined to the printed circuit board by way of an adhesive layer, wherein, for effective mechanical decoupling, the adhesive layer should have a sufficient thickness so as to prevent, in particular, that the sensor device possibly rests on protrusions or the like that exist at the printed circuit board within the scope of production subject to tolerances, which otherwise could be accompanied by undesirable mechanical coupling.

An approach is desirable in this regard in which the layer thickness of the adhesive layer can be set in a defined manner with sufficient process reliability.

An adhesive for bonding a semiconductor sensor to a substrate is known from European Published Application No. EP 3 428 600 A1. The adhesive is formed by a silicone adhesive, which comprises so-called spacers in the form of silicone particles.

U.S. Publication No. 2003/0043476 describes a joint between an optical device and a mounting plate.

The present disclosure is directed toward overcoming one or more of the above-mentions problems, though not necessarily limited to embodiments that do.

SUMMARY

It is an object of the present invention to provide a printed circuit board assembly, an implantable medical device, and a method for producing a printed circuit board assembly, which in a simple, inexpensive manner enable a joint between a sensor device and a printed circuit board for installation in a medical device, with advantageous mechanical decoupling and improved process reliability.

A printed circuit board assembly according to claim 1, an implantable medical device according to claim 10, and a method according to claim 11 are provided. Further embodiments are the subject matter of dependent claims.

According to a first aspect, a printed circuit board assembly of an implantable medical device is provided. The printed circuit board assembly comprises a printed circuit board and a sensor device arranged at the printed circuit board. The sensor device is joined to the printed circuit board by way of an adhesive layer. The adhesive layer is formed of an adhesive compound in which glass spheres are embedded.

The joint between the sensor device, which, in particular, is designed as a transducer for converting a pressure signal into an electrical signal, and the printed circuit board is achieved by way of an adhesive layer, which is produced from an adhesive compound mixed with glass spheres. The glass spheres have a defined size, in particular a diameter in a defined range, and are used as spacers in the adhesive compound so as to ensure that the adhesive layer cannot fall below a minimum thickness, and the sensor device is thus joined to the printed circuit board by way of an adhesive layer that is sufficiently thick for mechanical decoupling.

The glass spheres have a modulus of elasticity between 40,000 N/mm$^2$ and 90,000 N/mm$^2$ and are thus comparatively rigid and inelastic, so that the glass spheres do not yield, and also no deformation of the glass spheres can occur under comparatively high pressure when the sensor device is joined onto the printed circuit board.

The glass spheres can have a spherical shape having a circular cross-section. The shape of the glass spheres, however, may also deviate from an ideal spherical shape, for example in that the cross-section of the glass spheres is designed in a manner deviating from a circular shape, for example that these are elliptically shaped.

The glass spheres can, for example, have a diameter between 20 μm and 100 μm, for example between 25 μm and 80 μm, and preferably between 30 μm and 50 μm. Since the glass spheres have a diameter in a defined range, and the glass spheres thus preferably only differ to a minor degree in the diameters thereof, favorable, uniform support of the sensor device with respect to the printed circuit board can be created by way of the glass spheres in the adhesive layer, in particular along a normal direction perpendicular to the surface of the printed circuit board, along which the sensor device is placed onto the surface of the printed circuit board.

The proportion of the glass spheres in the adhesive layer can be between 5% by weight and 40% by weight, for example between 8% by weight and 20% by weight, for example 10% by weight. As a result of a sufficiently high proportion of glass spheres in the adhesive layer, a distributed support of the sensor device with respect to the printed circuit board can be created with a homogeneous distribution of the glass spheres in the adhesive layer and with a comparatively small distance between adjoining glass spheres, so that a defined intermediate layer is created between the sensor device and the printed circuit board, with an integral (adhesive) joint and a defined layer thickness.

The adhesive compound is preferably formed by an adhesive that is considerably softer than the glass spheres, even when cured. While the sensor device is thus supported, by way of the glass spheres, comparatively rigidly with respect to the printed circuit board along the normal to the printed circuit board surface, decoupling between the sensor device and the printed circuit board is created along the two other spatial directions which are parallel to the printed circuit board surface. Mechanical stresses, which act, in particular, horizontally along the printed circuit board and are caused, for example, by a deformation at the printed circuit board, thus cannot be transmitted to the sensor device along the plane of the printed circuit board, so that the sensor device is mechanically decoupled from the printed circuit board. In this way, a distortion of sensor signals, and in particular a drift of sensor signals, due to stresses and deformations at the printed circuit board is effectively prevented.

As a result of the elasticity of the adhesive compound, moreover stresses along the normal direction, caused by bending of the printed circuit board, for example, may also be compensated for so that such stresses cannot be transmitted directly to the sensor device and are at least substantially damped.

The adhesive compound can be formed by a silicone adhesive, for example. Such a silicone adhesive can have a high chain mobility of silicone polymers, which results in comparatively high elasticity, even of the cured adhesive compound. Such silicone adhesives can be heat-resistant and additionally resistant to UV radiation. Silicone adhesives can moreover be resistant to moisture.

Silicone adhesives can be used as 1-component or 2-component adhesive systems. Both 1-component systems and 2-component systems are based on polyorganosiloxanes, usually polydimethylsiloxanes, and cure by polycondensation.

In one embodiment, the sensor device is designed as a transducer for converting a pressure signal into an electrical signal. The sensor device can comprise a pressure membrane, for example, which can be brought in contact with a fluid and is thus able to absorb pressure in the fluid. As an alternative, the sensor device can have a piezoelectric design, for example, for converting a pressure signal into a correlated electrical signal.

In one embodiment, an implantable medical device comprises a printed circuit board assembly of the type described above. Such an implantable medical device comprises a housing in which the printed circuit board assembly is enclosed. The printed circuit board assembly is usually fixedly joined to the housing in the process and, in addition to the sensor device, comprises further electrical or electronic components by way of which signals can be processed, and in particular sensor signals received via the sensor device can be preprocessed.

The installation situation of the printed circuit board assembly into the implantable medical device can have a one-sided clamped design (similarly to a springboard). As an alternative, the installation situation can have a two-sided clamped design, which is simpler from a design perspective.

The printed circuit board assembly can comprise one or more FR4 printed circuit boards. The printed circuit board assembly can comprise one or more ceramic multilayer-based printed circuit boards (low temperature cofired ceramics, LTCC). A flexible printed circuit board responds to mechanical stresses by deforming, a kind of corrugation. In the region of the rigid transducer, these waves then result in stresses again. As a result, printed circuit boards that are as rigid as possible are to be preferred.

Such an implantable medical device can be designed as an implantable pressure sensor, for example, which can be implanted into a human vessel, in particular a blood vessel, so as to detect the pressure in the vessel, for example for monitoring the (local) blood pressure over an extended period of time. Such a medical device in the form of an implantable pressure sensor can, for example, be implanted in the region of the heart, for example intracardially. The pressure sensor can be connected to a likewise implanted control unit, which however is arranged outside the heart, by way of a lead. The control unit can comprise control electronics, for example, for evaluating sensor signals. The control unit can moreover comprise communication components, for example, via which signals can be transmitted to an external unit outside the patient, for example by way of telemetry. In another embodiment, the pressure sensor itself can comprise communication components and be configured to communicate wirelessly with a device situated outside the patient, for example so as to transmit data to the device and/or receive programming commands from the device. The device can be a smart phone or a tablet, for example.

An object is also achieved by a method for producing a printed circuit board assembly of an implantable medical device in which a sensor device is joined to a printed circuit board by way of an adhesive layer. The adhesive layer is formed of an adhesive compound into which glass spheres are mixed.

The advantages and advantageous embodiments described above for the printed circuit board assembly and the medical device are analogously applied to the method, so that reference is made to what was stated above in this regard.

The adhesive compound can, in particular, be a silicone adhesive, which can be present in the form of a 1-component adhesive system or a 2-component adhesive system. If the adhesive compound is a 2-component system, the components of the adhesive compound are preferably initially mixed with one another and only thereafter mix the glass spheres into the adhesive compound. Bubbles should be avoided during mixing so as to prevent air inclusions in the adhesive compound.

The glass spheres mixed into the adhesive compound preferably have a diameter in a defined range, such as between 20 µm and 100 µm, for example between 25 and 80 µm, and preferably between 30 and 50 µm. Such glass spheres can be obtained, for example, by sieving, in that a desired proportion of glass spheres having a diameter in a defined range is sieved and used exclusively for mixing with the adhesive compound.

So as to join the sensor device to the printed circuit board, the sensor device is placed onto the printed circuit board along the normal direction of the printed circuit board by means of an interposed adhesive compound that is mixed with the glass spheres. The sensor device is supported with respect to the printed circuit board by way of the glass spheres during joining in such a way that an adhesive layer having a defined thickness is obtained, which in particular does not fall below a minimum thickness predefined by the glass spheres.

Since the sensor device is rigidly supported along the normal to the printed circuit board surface by way of the glass spheres embedded to the adhesive layer, processes thereafter may be facilitated, in particular for electrically connecting the sensor device by way of bond pads on the top side thereof to the printed circuit board. For example, the sensor device can be connected to the printed circuit board by way of wire bonding in that one or more thin wires are connected to the sensor device and the printed circuit board so as to thereby achieve electrical contacting between the sensor device and the printed circuit board. The connection can be carried out, for example, using an ultrasonic wire bonding process in that wire connections or connecting wires are connected to the sensor device and the printed circuit board by way of ultrasonic welding. The rigid design along the normal to the printed circuit board surface ensures optimal force transmission in the process.

BRIEF DESCRIPTION OF THE DRAWINGS

The idea(s) underlying the present invention shall be described in greater detail hereafter based on the exemplary embodiments shown in the Figures. In the drawings.

Figure 1:
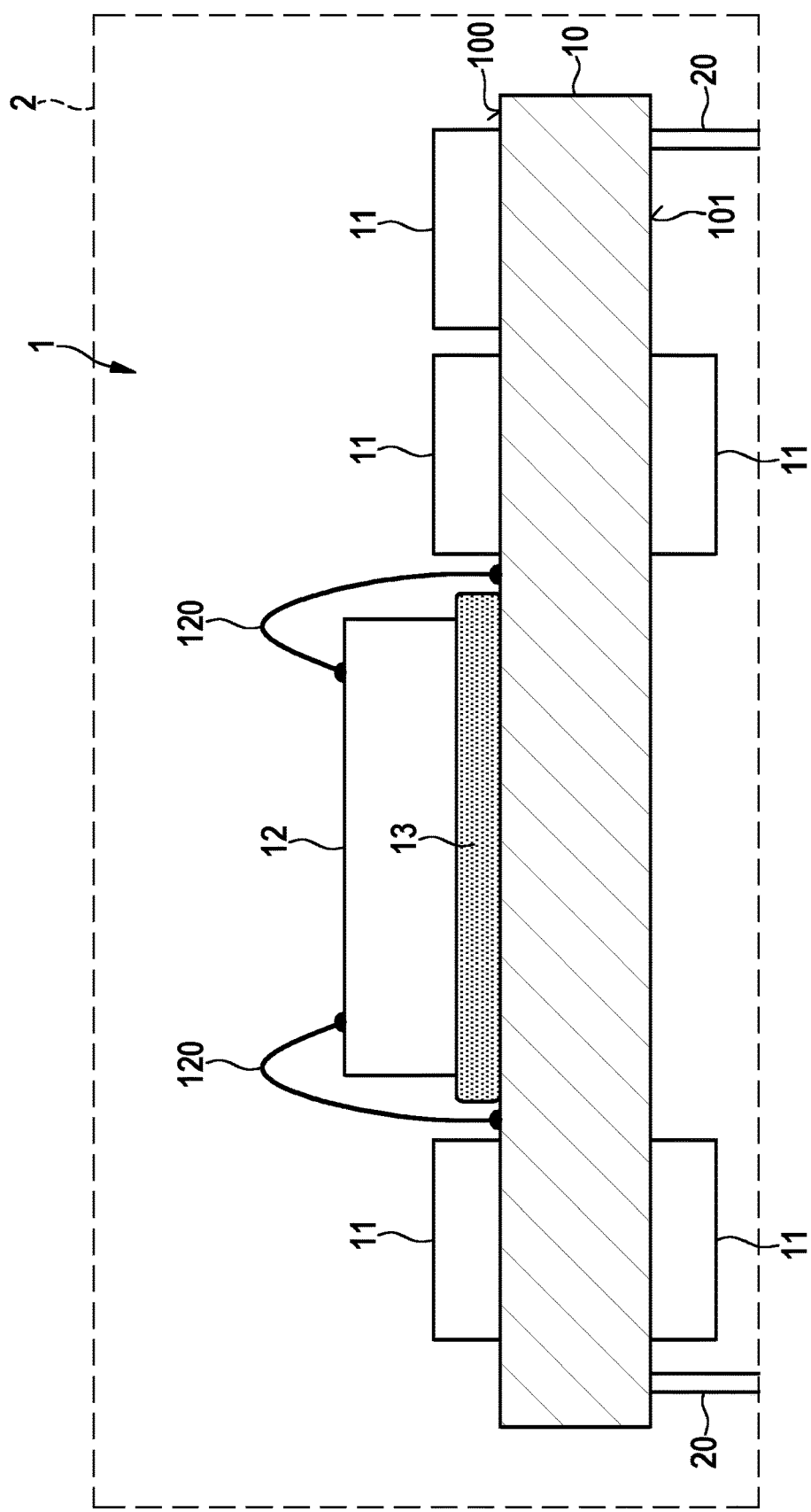
FIG. 1 shows a schematic view of a printed circuit board assembly, comprising a sensor device arranged at the printed circuit board.

A printed circuit board assembly 1 shown schematically in FIG. 1 is an integral part of a medical device, for example of an implantable pressure sensor, and is enclosed in a housing 2 of the implantable medical device.

Figure 5:
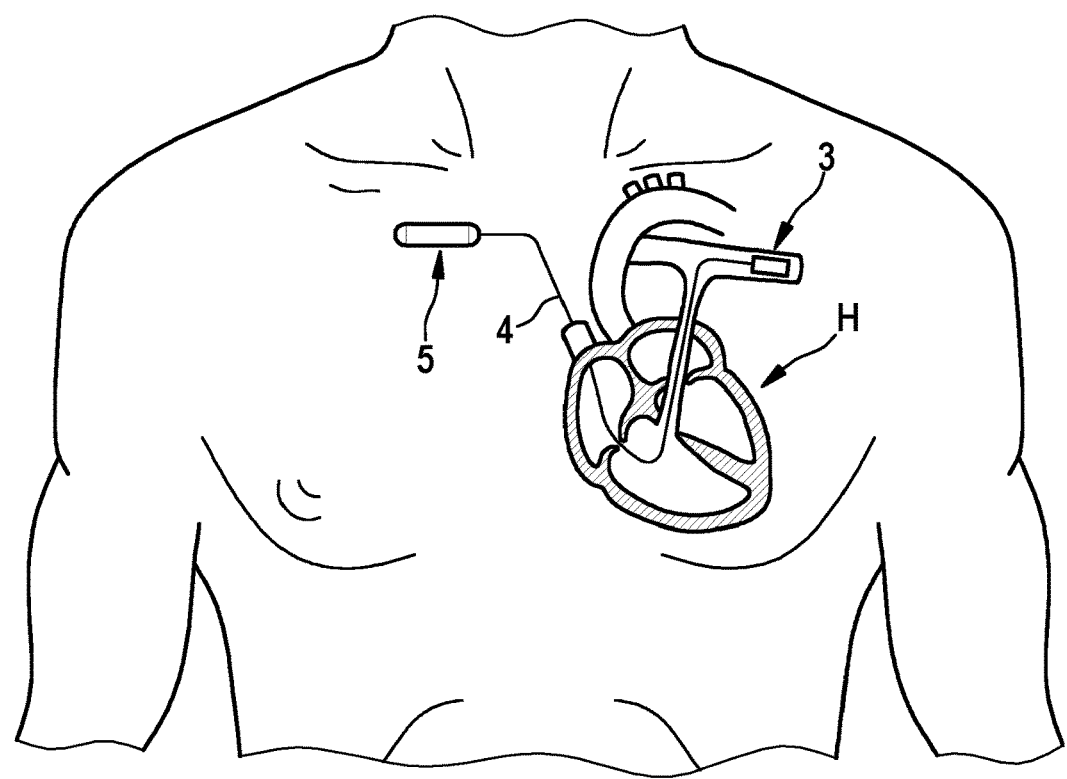
FIG. 5 shows a schematic view of an implantable medical device in a human body.

As is apparent from FIG. 5, such an implantable device can be implanted in the form of an implantable pressure sensor 3, for example, into a vessel in the region of the heart H of a patient, such as to measure a blood pressure in the region of the heart for the purpose of monitoring. The pressure sensor 3 is connected via a lead 4 to a likewise implanted control unit 5, which, for example, evaluates and processes sensor signals received from the pressure sensor 3 and, for example, communicates these to a higher-level, external unit outside the patient, using telemetry for example. As an alternative, the pressure sensor 3 can be designed to be wireless and transmit the sensor signals wirelessly to a device situated outside the body (such as a smart phone or a tablet) (not shown).

As is apparent from FIG. 1, the printed circuit board assembly 1 comprises a printed circuit board 10, which is connected to the housing 2 of the medical device by way of attachment devices 20 in the manner of fixed bearings. The printed circuit board 10 carries electrical and electronic components 11, for example a processor, an energy store in the form of a battery or the like, and/or passive electrical components, wherein such electrical and electronic components 11 can be arranged on sides 100, 101 of the printed circuit board 10 that face away from one another.

On a top side 100 of the two sides 100, 101 of the printed circuit board 10, moreover a sensor device 12 is arranged, which is joined to the printed circuit board 10 by way of an adhesive layer 13. Via wire connections 120 connected by way of wire bonding, for example, the sensor device 12 is connected to the printed circuit board 10, and in particular to conductors formed at the printed circuit board 10, so that the sensor device 12 is also electrically connected to the printed circuit board 10.

During operation, mechanical stresses can be transmitted from the housing 2 to the printed circuit board 10 via the attachment devices 20. So as to prevent such mechanical stresses from also being introduced from the printed circuit board 10 into the sensor device 12 and possibly resulting in mechanical deformation at the sensor device 12 (which otherwise could result in a distortion of sensor signals recorded by way of the sensor device 12), the adhesive layer 13, beyond the function thereof of integrally joining the sensor device 12 to the printed circuit board 10, also has the function of mechanically decoupling the sensor device 12 from the printed circuit board 10 in such a way that mechanical stresses, which act in particular parallel to the plane of the printed circuit board 10, cannot be directly transmitted to the sensor device 12.

Figure 2:
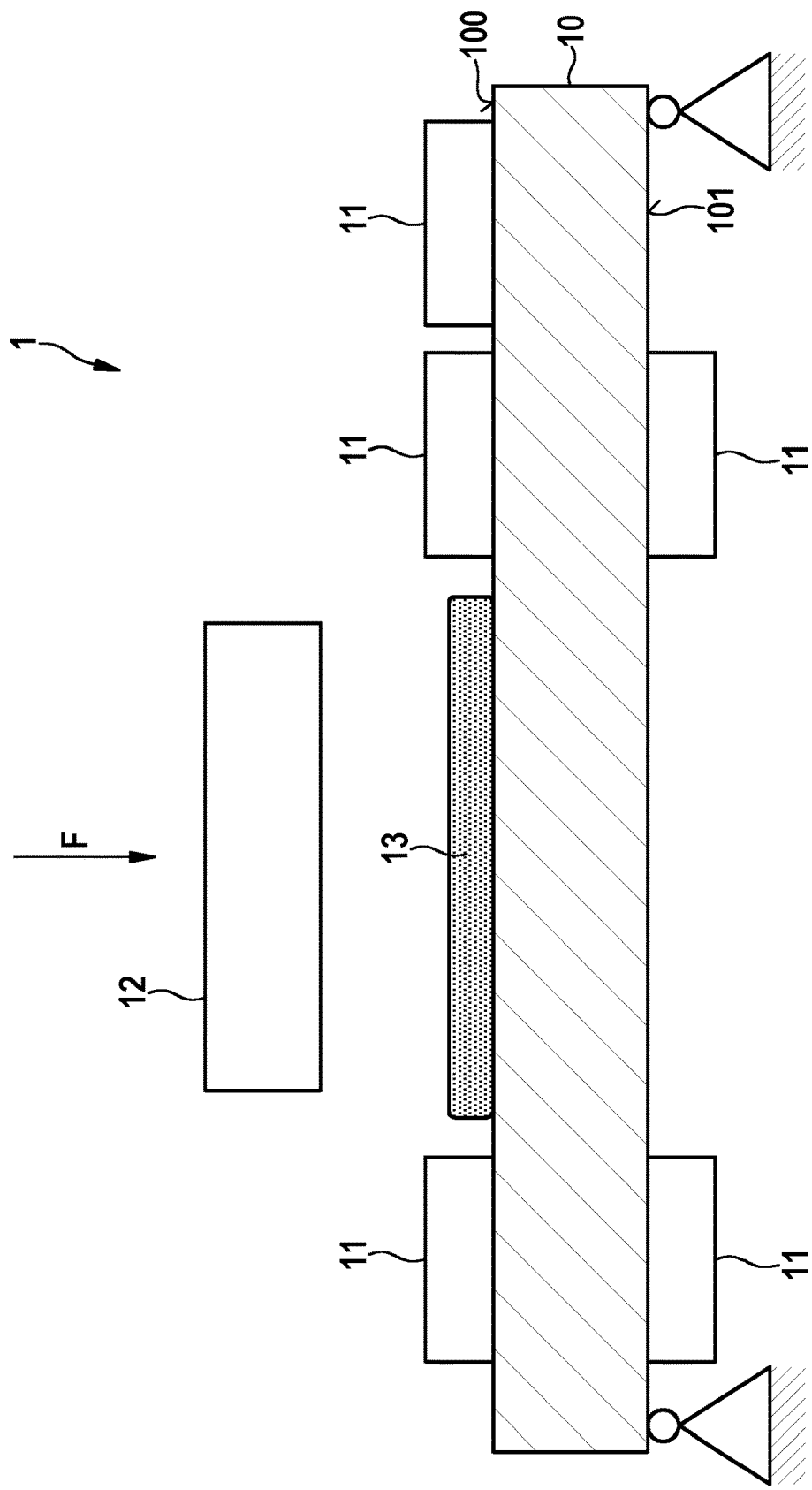
FIG. 2 shows a schematic view during joining of the sensor device to the printed circuit board.

As is shown schematically in FIG. 2, the sensor device 12, for the purpose of being joined to the printed circuit board 10, is placed onto the printed circuit board 10 along a joining direction F, which is oriented perpendicularly to the plane of the printed circuit board 10, and is integrally joined to the printed circuit board 10 by way of the adhesive layer 13 formed between the sensor device 12 and the printed circuit board 10. So as to achieve sufficient mechanical decoupling of the sensor device 12 from the printed circuit board 10, it is advantageous in the process to ensure that the adhesive layer 13 sufficiently thick, so that stresses are compensated for via the adhesive layer 13 and are not directly introduced from the printed circuit board 10 into the sensor device 12.

Figure 3:
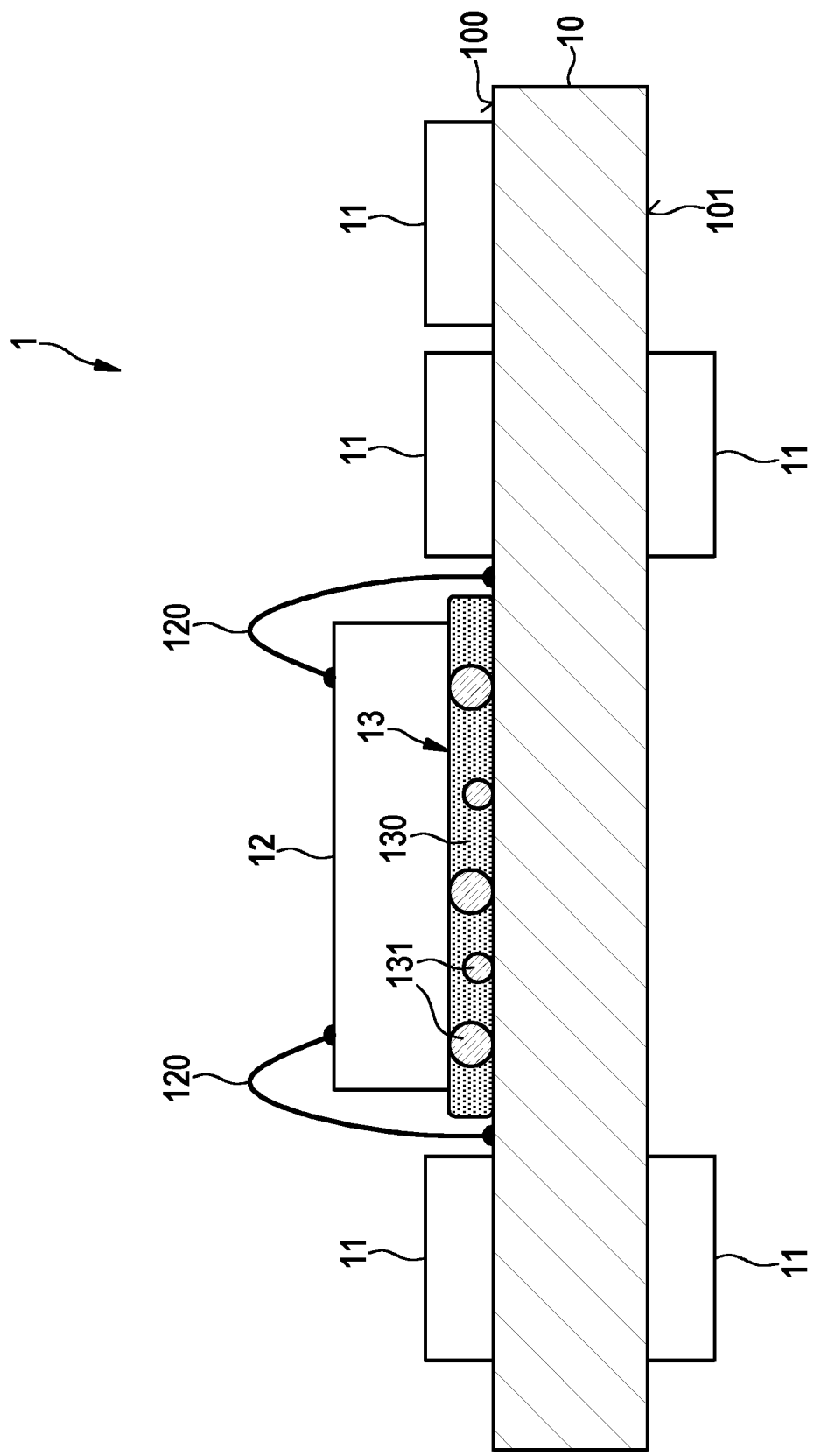
FIG. 3 shows a view of the printed circuit board assembly during joining of the sensor device.

For this purpose, in the exemplary embodiment shown in FIG. 3, the adhesive layer 13 is formed by an adhesive compound 130 in which glass spheres 131 having a diameter in a defined range are embedded. The adhesive compound 130 can, for example, be a silicone adhesive, for example a 2-component adhesive, which is mixed with the glass spheres 131 prior to being applied onto the printed circuit board 10, so that a composition comprising the adhesive compound 130 and the glass spheres 131 is obtained, and is applied onto the printed circuit board 10 so as to form the adhesive layer 13 prior to joining the sensor device 12.

Figure 4:
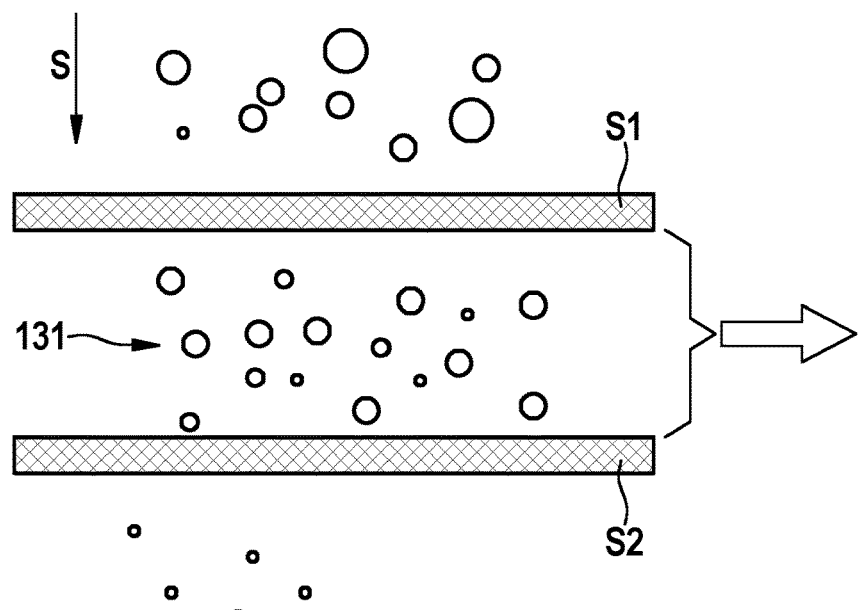
FIG. 4 shows a schematic view of a sieving of glass spheres for use with an adhesive compound for joining the sensor device.

The glass spheres 131 preferably have a diameter in a range between 20 μm and 100 μm, for example between 25 μm and 80 μm, and preferably between 30 μm and 50 μm. For this purpose, glass spheres 131 can be sieved using sieves S1, S2, as is shown schematically in FIG. 4, so that a proportion of glass spheres 131 having a diameter in a desired, defined range is obtained. This can take place, for example, in that a first sieve S1 (as viewed along a sieving direction S), has a mesh size corresponding to the upper limit of the desired diameter range, and a second sieve S2, which is arranged downstream of the first sieve S1 in the sieving direction S, has a mesh size corresponding to the lower limit of the diameter range. Glass spheres 131 that pass the first sieve S1, but are collected at the second sieve S2 have a diameter in the desired diameter range.

Such glass spheres 131 have a modulus of elasticity between 40,000 N/mm$^2$ and 90,000 N/mm$^2$ and are thus comparatively rigid. The sensor device 12 is thus supported with respect to the printed circuit board 10 by way of the glass spheres 131 along the normal direction, that is, perpendicularly to the printed circuit board 10, in a comparatively rigid manner.

In contrast, the adhesive compound 130, composed of the silicone adhesive, is comparatively soft and elastic, so that the sensor device 12 is elastically decoupled from the printed circuit board 10, in particular in spatial directions parallel to the plane of the printed circuit board 10. Mechanical stress forces that are directed horizontally with respect to the printed circuit board 10 thus cannot be (directly) transmitted from the printed circuit board 10 onto the sensor device 12, but are damped and thus do not distort sensor signals.

The sensor device 12 being supported with respect to the printed circuit board 10 by way of the glass spheres 131 along the normal direction of the printed circuit board 10 has the further advantage that process steps to be performed after the sensor device 12 has been joined to the printed circuit board 10 can be carried out with improved process reliability. In this way, wire connections 120 can be connected to the sensor device 12 and the printed circuit board 10 by way of wire bonding, for example by way of ultrasonic wire bonding, so as to electrically connect the sensor device 12 to the printed circuit board 10. Mechanical forces that are introduced into the sensor device 12 for bonding the wire connections 120 to the sensor device 12 are transmitted by way of the (rigid) glass spheres 131.

The idea(s) underlying the invention is not limited to the above-described exemplary embodiments, but can also be implemented in another manner.

In principle, the use of an adhesive layer, which is composed of an adhesive compound and glass spheres embedded therein, is not limited to the attachment of a sensor device for the conversion of a pressure signal into an electrical signal, but other sensor devices can also be joined to a printed circuit board by way of such an adhesive layer.

A printed circuit board assembly of the described kind can be integrated in a wide variety of implantable medical devices, for example implantable pressure sensors, cardiac pacemakers or defibrillators and the like.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this disclosure, which is to be given the full breadth thereof. Additionally, the disclosure of a range of values is a disclosure of every numerical value within that range, including the end points.

LIST OF REFERENCE SIGNS 1 printed circuit board assembly
10 printed circuit board
100 top side
101 bottom side
11 electronic component
12 sensor device (transducer)
120 wire connection
13 adhesive layer
130 adhesive compound
131 glass spheres
2 housing
20 attachment device
3 implantable pressure sensor
4 lead
5 control unit
F joining direction
H heart
S sieving direction
S1, S2 sieve

What is claimed is:

1. A printed circuit board assembly of an implantable medical device, comprising:
   a printed circuit board, and
   a sensor device that is arranged at the printed circuit board and joined to the printed circuit board by way of an adhesive layer, wherein the adhesive layer is formed of an adhesive compound in which glass spheres are embedded,
   wherein the glass spheres have a modulus of elasticity between 40000 N/mm$^2$ and 90000 N/mm$^2$,
   wherein the glass spheres have a diameter between 30 μm and 50 μm,
   wherein the proportion of the glass spheres in the adhesive layer is between 8% by weight and 20% by weight, and
   wherein the sensor device is a transducer for converting a pressure signal into an electrical signal.

2. The printed circuit board assembly according to claim 1, wherein the adhesive compound is formed by a silicone adhesive.

3. An implantable medical device comprising a printed circuit board assembly according to claim 1.

4. A method for producing a printed circuit board assembly of an implantable medical device, comprising:
   joining a sensor device to a printed circuit board by way of an adhesive layer, wherein the adhesive layer is formed of an adhesive compound into which glass spheres are mixed,
   wherein the glass spheres have a modulus of elasticity between 40000 N/mm$^2$ and 90000 N/mm$^2$,
   wherein the glass spheres have a diameter between 30 μm and 50 μm,
   wherein the proportion of the glass spheres in the adhesive layer is between 8% by weight and 20% by weight, and
   wherein the sensor device is a transducer for converting a pressure signal into an electrical signal.

5. The method according to claim 4, wherein the adhesive compound is mixed from two components of a silicone adhesive, and the glass spheres are mixed into the adhesive compound after the adhesive compound has been mixed.

6. The method according to claim 4, wherein wire connections are connected to the sensor device by way of wire bonding after the sensor device has been joined to the printed circuit board.

* * * * *